United States Patent [19]

Guarino et al.

[11] Patent Number: 5,239,997
[45] Date of Patent: Aug. 31, 1993

[54] DIAGNOSTIC APPARATUS UTILIZING LOW FREQUENCY SOUND WAVES

[76] Inventors: John R. Guarino; Joseph C. Guarino, both of 2404 Ormond St., Boise, Id. 83705; Louis J. Guarino, P.O. Box 164, Washingtonville, N.Y. 10992

[21] Appl. No.: 632,111
[22] Filed: Dec. 20, 1990
[51] Int. Cl.⁵ ............................................. A61B 5/02
[52] U.S. Cl. .................................. 128/630; 128/774
[58] Field of Search ............... 128/715, 630, 773–774; 181/126

[56] References Cited

U.S. PATENT DOCUMENTS

| | | | |
|---|---|---|---|
| 4,672,977 | 6/1987 | Kroll | 128/773 X |
| 4,819,753 | 4/1989 | Higo et al. | 128/773 |
| 5,024,239 | 6/1991 | Rosenstein | 128/773 X |
| 5,115,813 | 5/1992 | Ylander et al. | 128/660.01 |

*Primary Examiner*—Francis Jaworski
*Attorney, Agent, or Firm*—McGlew & Tuttle

[57] ABSTRACT

A diagnostic apparatus for producing low frequency sound waves applied to a structure to be examined to induce sound waves in the structure and a sensor which is positioned on the structure remote from the sound producing means to receive the sound waves after passage through the structure and to convert the sound waves into electrical impulses. The sensor is connected to an amplifier to boost the electrical signals and transmit the same to a computer data processor and receiver unit for storing the signals and converting the signals into a visual form.

20 Claims, 3 Drawing Sheets

DIAGNOSTIC APPARATUS UTILIZING LOW FREQUENCY SOUND WAVES

This invention relates in general to a diagnostic apparatus for the detection and quantification of abnormalities or defects in a living body, and more particularly, to a diagnostic apparatus employing low frequency sound waves.

BACKGROUND OF THE INVENTION

Heretofore, physical examination of the human body for abnormalities, as for example, extradural and subdural hematomas, lesions and other masses, has been accomplished by the use of expensive and/or invasive diagnostic equipment. Three examples of such equipment, in addition to X-rays, are the computer tomography (CT) scanner, the magnetic resonance imaging (MRI) and the positron emission tomography device, each of which are employed to provide an image of a patient's tissue. Because of the cost and the technical complexity, the availability of such equipment is limited to major hospitals and clinics. Where X-ray equipment is used, it must be employed in a guarded environment to protect the operating technician and the patient from radio-active contamination and therefore is relatively costly. Another expensive diagnostic apparatus in common use employs ultra-high frequency sound; that is sound of a frequency above that audible by the human ear, which is in the range of 20,000 vibrations per second and above. This procedure has not proven entirely satisfactory for the detection of brain abnormalities because the short length of the ultra-high frequency wave is scattered by the bone structure of the head whereas diagnosis depends upon reception of the sound wave along the same axial path as the applied sound wave.

A non-invasive and inexpensive method of detecting the presence of an abnormality in the human body is known as auscultatory percussion. This method consists of applying a low frequency sound wave directly to the body such as the head or breast bone by finger tapping, a vibrator, or a sound generator. A stethoscope is applied successively from one side to the opposite side of the head or in the case of a chest examination to successive areas of the posterior chest wall to discern whether or not there is any diminished resonance or dullness. A change in the intensity of the sound is an indication of an abnormality since sound waves are attenuated by a medium of different density and/or physical character lying within an otherwise uniform material. Less sound energy is transmitted through the diseased area when compared to the opposite uninvolved area of the head or chest. The change in sound energy is measurable and enables detection and monitoring of the progress of disease in response to treatment. This concept was developed and applied by one of the co-inventors in his examination for diagnosing brain disease. By tapping with the pulp of his finger at a marked point in the midline of the upper forehead above the frontal sinuses, and applying the stethoscope alternately from one side to the opposite side of the head at corresponding anatomical areas, the inventor was able to determine and compare differences in sound between the opposite sides of the head.

The inventor also applied his method of auscultatory percussion in diagnosing chest disease by tapping lightly on the patient's breast bone with his finger, while listening with the stethoscope applied to the posterior chest wall. Percussion is applied with equal intensity over the same area of the breast bone, while the stethoscope explores both lung fields systematically to detect differences in sound transmission. In a controlled blind study of 28 patients with prominent chest disease determined by X-rays, each had normal or equivocal findings by conventional methods of percussion. In each of the 28 patients lung abnormality was readily detected by the author's method of auscultatory percussion.

SUMMARY AND OBJECT OF THE INVENTION

The present invention therefore, contemplates an improved diagnostic apparatus for the detection and quantification of abnormalities or diseases and defects in a living body which comprises a means for inducing, in the body to be examined, a low frequency sound wave, as for example by direct percussion on the part of the body to be examined, and a sensing means applied to that part of the body remote from the first mentioned means for receiving the induced low frequency sound wave after it has passed through the body and to convert the sensed sound wave into an output electrical signal proportionate to the sensed sound wave. The apparatus also includes a computerized data processing and receiving unit connected to the sensing means for receiving electrical signals from the latter and storing and converting the signals into a visual display.

In a narrower aspect of the present invention the first mentioned means includes a signal generator which generates and amplifies an electrical current proportionate to the desired low frequency sound wave to be applied and a receiver for converting the electrical current received from the signal generator into a low frequency sound wave against the body part to be examined.

It is therefor an object of this invention to provide a diagnostic apparatus employing low frequency sound waves for detecting and quantifying abnormalities or defects in a living body which is small in size, readily portable, and inexpensive to use.

Another object of the present invention is to provide a diagnostic apparatus employing low frequency sound waves for detecting and quantifying abnormalities or defects in a living body which is simple to use and more accurate than present known sonic equipment and techniques.

The present invention also provides a diagnostic apparatus which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
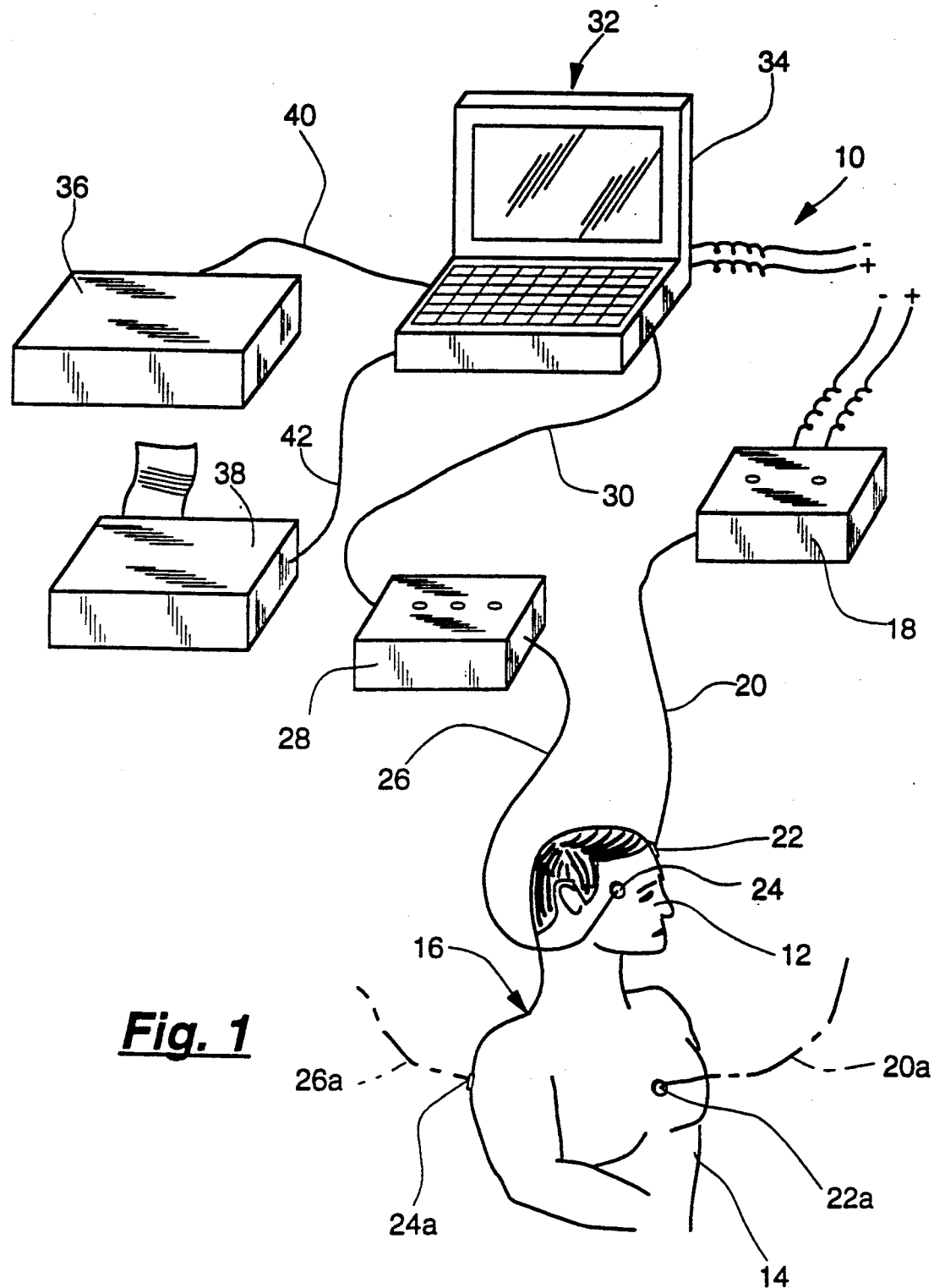
FIG. 1 is a diagrammatic showing of the diagnostic apparatus according to this invention.

Now referring to FIG. 1, the reference number 10 generally designates the diagnostic apparatus according to this invention as used for the examination of the head 12 and/or chest 14 of a patient 16.

It is to be understood that while the diagnostic apparatus 10 is shown and will be described as being used for the examination of the head and chest of a patient 16, the invention is not limited thereto.

The diagnostic apparatus 10 comprises a signal generator 18 which is connected to a source of electrical power and functions to generate an amplified electrical current proportional to a desired sound wave frequency. The signal generator 18 may be of the type manufactured by Dynascan Corporation of Chicago, Ill., designated as model 3020 Sweep/Function generator and which is electrically attached by a coaxial cable to a stereo amplifier, Model SA-15, sold by Tandy Corporation of Ft. Worth, Tex., under the trademark "Realistic". The signal generator 18 is connected, through a flexible conduit 20, to a transmitting means 22 (hereinafter referred to as the transmitting transducer).

The transmitting transducer 22 is similar to a telephone receiver which converts the electrical current received from signal generator 18 into sound waves of a frequency determined by the electric current transmitted through conduit 20. The transmitting transducer 22 may be similar or equal to a speaker as manufactured by Fuji and sold by RJM Electronics, Boise, Id. As shown, transmitting transducer 22 is placed firmly against the head 12 of the patient 16 above the sinuses, if the brain is to be examined, or if the lungs are to be examined, against the breast bone as is shown by the dot-dash lines 20A and 22A. To receive the induced low frequency sound waves after passage through the body portion under examination, a sensor 24, having a thin flexible diaphragm that is readily responsive to the vibratory movement of the surface with which it is in direct contact, is placed firmly against the patient's head 12 at a point remote from transmitting transducer 22, or, in the case of a chest examination, against the posterior side of the chest as shown by dot-dash lines 26A and 24A. The sensor 24 is equipped with a microphone element that converts sound waves into electrical impulses or signals. The sensor 24 thus receives the induced sound waves after it has passed through the patient's tissues and converts the sound waves into electrical impulses or signals which are transmitted by a flexible conduit 26 to a signal amplifier 28.

The signal amplifier 28 amplifies the relatively weak electrical signal transmitted by sensor 24 and transmits the amplified electrical signal, via conduit or line 30, to a computer data processor and receiver unit 32. The signal amplifier 28 may be of any suitable type. One such high-gain operational amplifier is manufactured by Willmorth Engineering of Boise, Id., which utilizes voltage supplied by two nine volt batteries.

The computer data processor and receiver unit 32 (hereinafter referred to as the "computer unit") may be any well known computer unit suitably programmed to receive and process the amplified electrical impulses received via line 30. The computer unit 32 may be a computer manufactured by Apple Computer, Inc. of Cupertino, Calif. and designated Model IIe, which is modified to use a digital memory oscilloscope card, model 85, manufactured by Northwest Instruments Systems, Inc. of Beaverton, Oreg., which contains a high speed analog-to-digital converter which converts a continuous stream of analog information from signal amplifier 28 into digital data that the Model IIe computer is programmed to process.

Also forming part of the computer unit 32 is a monitor screen 34 where the received impulses consisting of the data is displayed to permit easy monitoring of the examination as it progresses. The monitor screen 34 may be of the type manufactured by Apple Computer, Inc. and designated "Monitor II". In addition, the computer unit 32 may include a mass storage device 36 and a printer 38 electrically connected, via lines 40 and 42, to the computer unit, respectively. The mass storage device 36 may be a tape recorder or disc drive. One such storage device is manufactured by Apple Computer, Inc. and is of the disc drive type that stores data onto a 5¼ inch floppy diskette. A suitable printer is currently manufactured by Epson, Inc. and designated Model RX-80 Dot Matrix.

Figure 2:
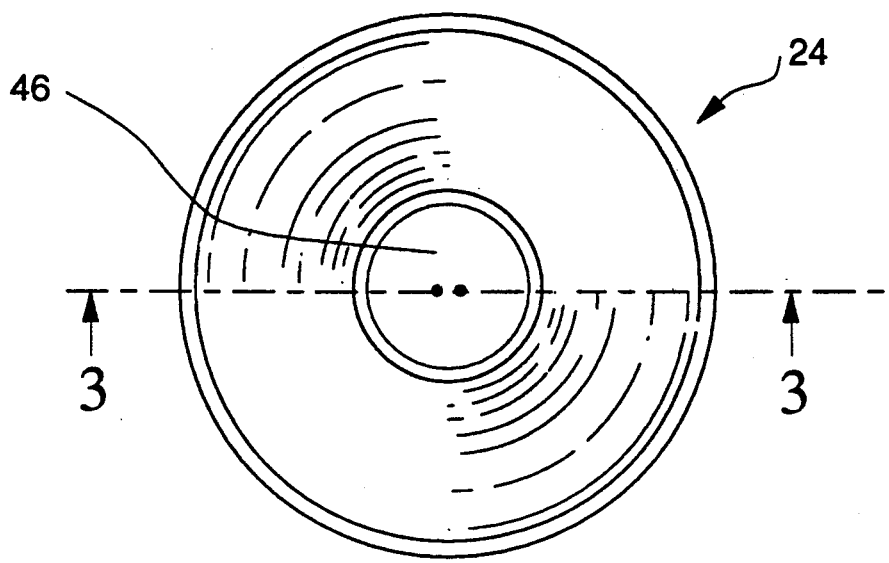
FIG. 2 is a diagrammatic showing of a plan view of the sensor used in FIG. 1.
Figure 3:
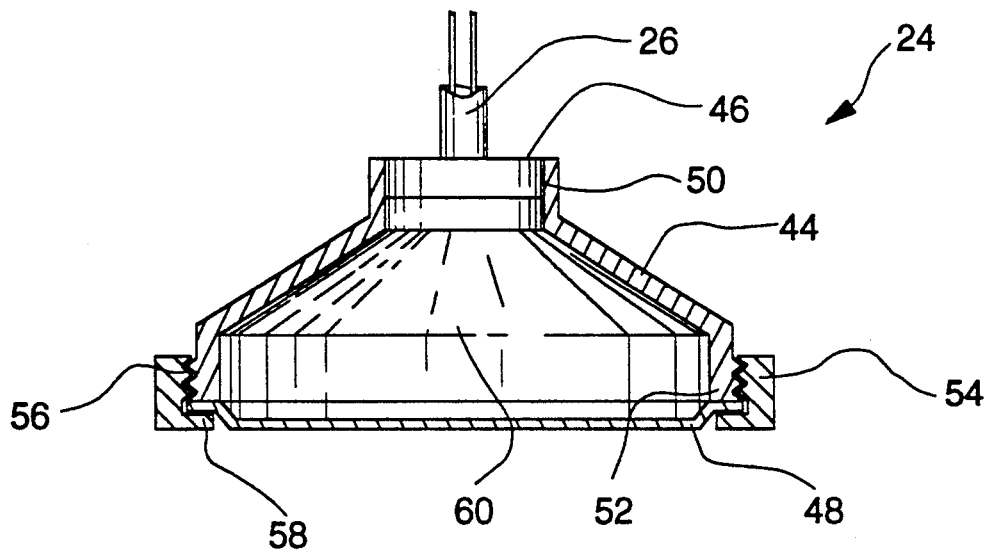
FIG. 3 is a cross-sectional view taken along the line A—A of FIG. 2.

Now referring to FIG. 2 and FIG. 3, the reference number 24 generally designates the sensor used in this invention. Sensor 24 comprises essentially a housing 44, a receiving transducer 46, and a flexible diaphragm 48. The housing 44 is generally bell-shaped and is open at the small diameter end portion 50 and open at the large diameter end portion 52. The receiving transducer 46 is secured within the small diameter open end portion 50 of housing 44, while flexible diaphragm 48 is secured within the large diameter open end portion 52 of housing 44. Flexible conduit 26 transmits the electrical impulse or signal from receiving transducer 46 to the signal amplifier 28 in FIG. 1. The receiving transducer 46 may be similar or equal to Archer Cat. No. 270-092B Mike element manufactured by Tandy Corp., Fort Worth, Tex. The receiving transducer 46 is secured within housing 44 in a fluid-tight manner, as for example by a flexible adhesive such as rubber cement, or a gasket made of rubber or similar material disposed between the open end portion 50 and receiving transducer 46. The diaphragm 48 is also secured in housing 44 in a fluid-tight manner. The diaphragm 48 is made of thin, flexible, impermeable material and may be made of plastic, animal skin, metal, or a combination of materials which will readily oscillate when sensing vibratory motion. As shown in FIG. 3, diaphragm 48 is clamped to the open end portion 52 of housing 44 by a threaded retaining ring 54 which is turned upon external threads 56 formed on end portion 52. To insure a fluid-tight seal around the periphery of diaphragm 48, a flexible adhesive or a gasket may be disposed between the diaphragm and the joining parts. Thus, the diaphragm 48 and receiving transducer 46 define within the housing 44 a hermetically sealed air chamber 60. Other known means may be used to secure diaphragm 48 and receiving transducer 46 to housing 44 such as, crimping, die-forming, bonding, and swaging.

In the use of sensor 24, the diaphragm 48 is placed against a surface as in FIG. 1, the vibration of which is to be sensed and measured. This contact or abutment of diaphragm 48 against the vibrating surface induces a like vibration or oscillation of diaphragm 48. The vibration in turn generates within the hermetically sealed air chamber 60 molecular activity, or energy or pressure waves of essentially the same magnitude and frequency as the magnitude and frequency of the vibration of diaphragm 48. The waves propagate through the hermetically sealed air chamber 60 unimpededly to impinge receiving transducer 46, thus, receiving transducer 46 converts the energy or pressure waves impinged upon it to a voltage of a value directly proportional to the magnitude and frequency of the energy or pressure waves. The voltage is then processed as shown in FIG. 1 into numerical values of vibration.

Figure 4:
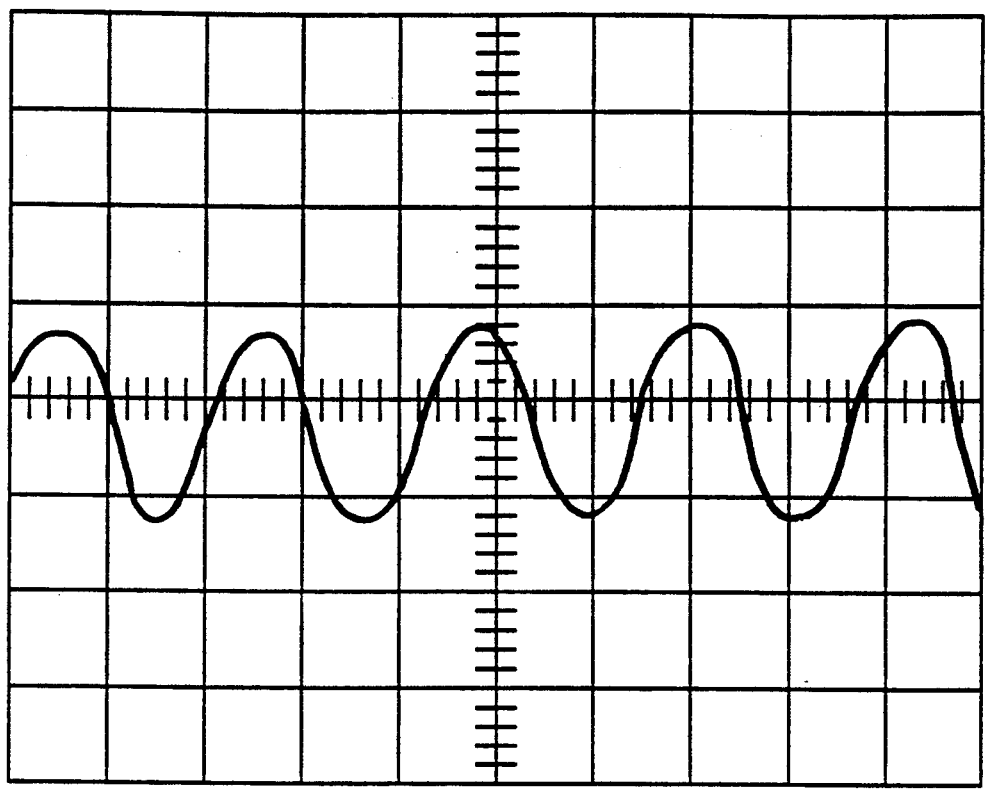
FIG. 4 is a visual representation provided by the computer data processor and receiver unit forming part of the apparatus shown in FIG. 1 of a low frequency sound wave pattern after it has passed through a brain-half free of abnormalities.
Figure 5:
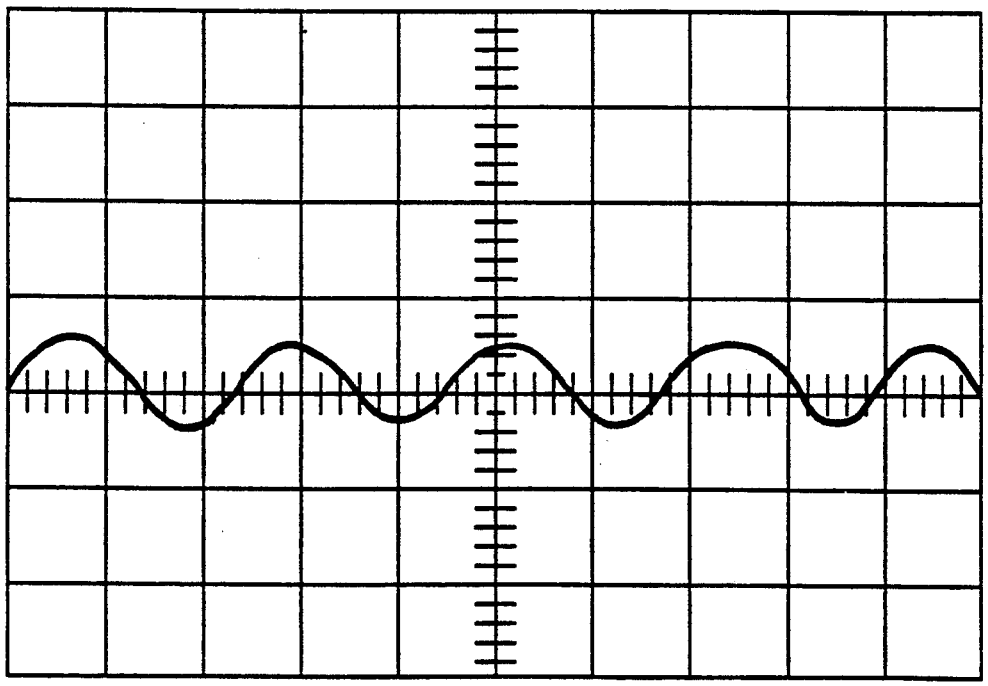
FIG. 5 is a Figure similar to FIG. 4 showing a visual representation of a low frequency sound wave pattern after it has passed through a brain-half having a diseased tissue of the same brain providing the display shown in FIG. 4.

In the use of diagnostic apparatus 10, the computer unit 32 and signal generator 18 are turned-on by actuation of a switch or switches (not shown) after the signal generator 18 has been adjusted to produce an electrical impulse required to produce the desired low frequency sound wave for the examination to be performed. Of course, the computer unit has also been programmed for the examination which is to be performed. If the examination is to be of the brain of patient 16, transmitting transducer 22 is held firmly against the forehead 12 of the patient. The sensor 24 is then placed alternately on each of the opposite sides of the patient's head 12 distal to the temporal line of the forehead along an imaginary horizontal line above the ear that extends from the temporal line of the forehead towards the occiput to receive at each location the sound wave that is transmitted through brain tissue. If the data or readings sensed by sensor 24 and transmitted to computer unit 32, via amplifier 28 and lines or conduits 26 and 30, are different as shown in FIGS. 4 and 5, diseased tissue has been detected. For an examination directed to the lungs of patient 16, transmitting transducer 22A is pressed firmly against the breast bone and the sensor 24A is applied to the posterior side of the patient's chest cavity at various locations in a systematic traverse of the entire lung area. Here again, if the data or readings are different as shown by a comparison of FIGS. 4 and 5, and as displayed on monitor 34, diseased tissue has been detected.

The aforesaid use of diagnostic apparatus 10 is applicable to the examination of organs of the body other than the brain and lungs of a living body. Malfunction of the bladder, and bone fractures are also discernable by use of diagnostic apparatus 10. The diagnostic apparatus 10 may also be employed to monitor the progress of healing of diseased tissues and fractures during therapy.

It is now readily apparent that an improved diagnostic apparatus employing low frequency sound waves has been provided which is simple and inexpensive while at the same time being very reliable in the detection of abnormalities and quantification of defects in a living body. It is an apparatus which is easy to use and does not require highly skilled technicians to operate and interpret the resultant data.

Although but one embodiment has been illustrated and described in detail, it is to be expressly understood that the invention is not limited thereto. Various changes can be made in the arrangement of parts without departing from the spirit and scope of the invention, as the same will now be understood by those skilled in the art.

What is claimed is:

1. A head diagnostic apparatus for detection and quantification of brain disease, the apparatus comprising:
   inducing means for inducing a low frequency vibration simultaneously and symmetrically through both halves of the brain, said inducing means being specifically formed for applying said low frequency vibration to the mid line of the upper part of the forehead above the frontal sinuses that extend approximately 3.5 cm above the supraorbital ridge;
   sensing means for receiving said low frequency vibration after it has passed through the head, and for converting said received low frequency vibration into an electrical signal proportionate to said received low frequency vibration, said sensing means being formed for receiving said low frequency vibrations by, methodical application upon correspondingly substantially opposite sides of the head, upon a line extending above ears posteriorly toward the temporal line of the forehead anteriorly, said sensing means being separately movable from said inducing means; and
   computerized data processing and receiving means for receiving said electrical signal from said sensing means and for storing and converting said electrical signal into a visual form, said computerized data processing and receiving means also comparing an electrical signal received on one of said opposite sides with another electrical signal received on another one of said opposite sides for the detection and quantification of brain disease in a portion of the brain through which said low frequency vibration is induced.

2. The apparatus of claim 1, wherein:
   said inducing means includes a signal generating means for producing an input electrical current proportionate to said induced low frequency vibration and a receiving means connected to said signal generating means to receive said input electrical current and to convert said input electrical current into said induced low frequency vibration for applying against the body to be examined.

3. The apparatus of claim 2, wherein:
   said inducing means includes a conduit and a transmitting transducer connected to a distal end of said circuit.

4. The apparatus of claim 3, wherein:
   an amplifier is connected to said sensing means and to said computerized data processing and receiving means, in order to receive said electrical signal from said sensing means and to amplify said electrical signal and transmit said amplified electrical signal to said computerized data processing and receiving means.

5. The apparatus of claim 4, wherein:
   said sensing means is connected by a flexible conduit to said amplifier to facilitate movement from one location on the body to another.

6. The apparatus of claim 5, wherein:
   a data storage device is connected to said computerized data processing and receiving means.

7. The apparatus of claim 6, wherein:

said computerized data processing and receiving means includes a monitor display screen and printing unit.

8. A chest diagnostic apparatus for detection and quantification of lung disease, the apparatus comprising:

inducing means for inducing a low frequency vibration simultaneously and symmetrically throughout both halves of the chest, said inducing means being specifically formed for anteriorly applying said low frequency vibration to a substantial center of the manubrium of the chest;

sensing means for receiving said low frequency vibration after said low frequency vibration has passed through the chest, said sensing means receiving said low frequency vibration from methodical application of said sensing means to a posterior chest wall and systematical exploration of both lung fields, and said sensing means converting said received low frequency vibration into an electrical signal proportional to said received low frequency vibration, said sensing means being separately movable from said inducing means; and computerized data processing and receiving means for receiving said electrical signal from said sensing means and for storing and converting said electrical signal into a visual form, said computerized data processing and receiving means also comparing different electrical signals received during said methodical application and exploration for the detection and quantification of lung disease in a portion of the lung through which said low frequency vibrations are induced.

9. The apparatus of claim 8, wherein:

said inducing means includes a signal generating means for producing an input electrical current proportionate to said induced low frequency vibration and a receiving means connected to said signal generating means to receive said input electrical current and to convert said input electrical current into said induced low frequency vibration for applying against the body to be examined.

10. The apparatus of claim 9, wherein:

said inducing means includes a conduit and a transmitting transducer connected to a distal end of said conduit.

11. The apparatus of claim 10, wherein:

an amplifier is connected to said sensing means and to said computerized data processing and receiving means, in order to receive said electrical signal from said sensing means and to amplify said electrical signal and transmit said amplified electrical signal to said computerized data processing and receiving means.

12. The apparatus of claim 11, wherein:

said sensing means is connected by a flexible conduit to said amplifier to facilitate movement from one location on the body to another.

13. The apparatus of claim 12, wherein:

a data storage device is connected to said computerized data processing and receiving means.

14. The apparatus of claim 13, wherein:

said computerized data processing and receiving means includes a monitor display screen and printing unit.

15. A diagnostic apparatus for detection and quantification of abnormalities and defects in a body to be examined, the apparatus comprising:

an inducing means for substantially transmitting a low frequency vibration in a plurality of substantially symmetrical paths through the body;

sensing means for separately receiving said low frequency vibration after being passed through the body along each of said plurality of substantially symmetrical paths, said sensing means being separately movable from said inducing means; and processing means for comparing a first low frequency vibration received along a first of said plurality of paths with a second low frequency vibration received along a second of said plurality of paths, said first path being substantially symmetrical to said second path, and said processing means displaying differences between said first and second low frequency vibrations caused by an abnormality in one of said first and second paths.

16. An apparatus in accordance with claim 15, wherein:

said inducing means has a transmitting transducer and said transmitting transducer receives a generated signal and converts said generated signal into said low frequency vibration, said low frequency vibration being proportional to said generated electrical signal;

said sensing means also converting each of said separately received low frequency vibrations into a separate received electrical signal proportionate to said each of said separately received low frequency vibrations, each of said separate received electrical signals being sent to said processing means; and said processing means having a signal generator creating said generated electrical signal, said generated electrical signal being generated with predetermined characteristics, and said processing means sending said generated signal to said inducing means at a predetermined time, said processing means comparing said each of said received electrical signals in one of a side by side, and one after another comparison.

17. An apparatus in accordance with claim 15, wherein:

said sensing means has a microphone element that is separately spaced at an end point of each of said plurality of substantially symmetrical paths.

18. An apparatus in accordance with claim 15, wherein:

said processing means detects a difference in attenuation between said first and second low frequency vibrations caused by one of said first and second low frequency vibrations passing through said abnormality.

19. An apparatus in accordance with claim 15, wherein:

said low frequency vibration is a low frequency sound wave.

20. An apparatus in accordance with claim 15, wherein:

said low frequency vibration is a plurality of low frequency sound waves.

* * * * *